Figure 1:
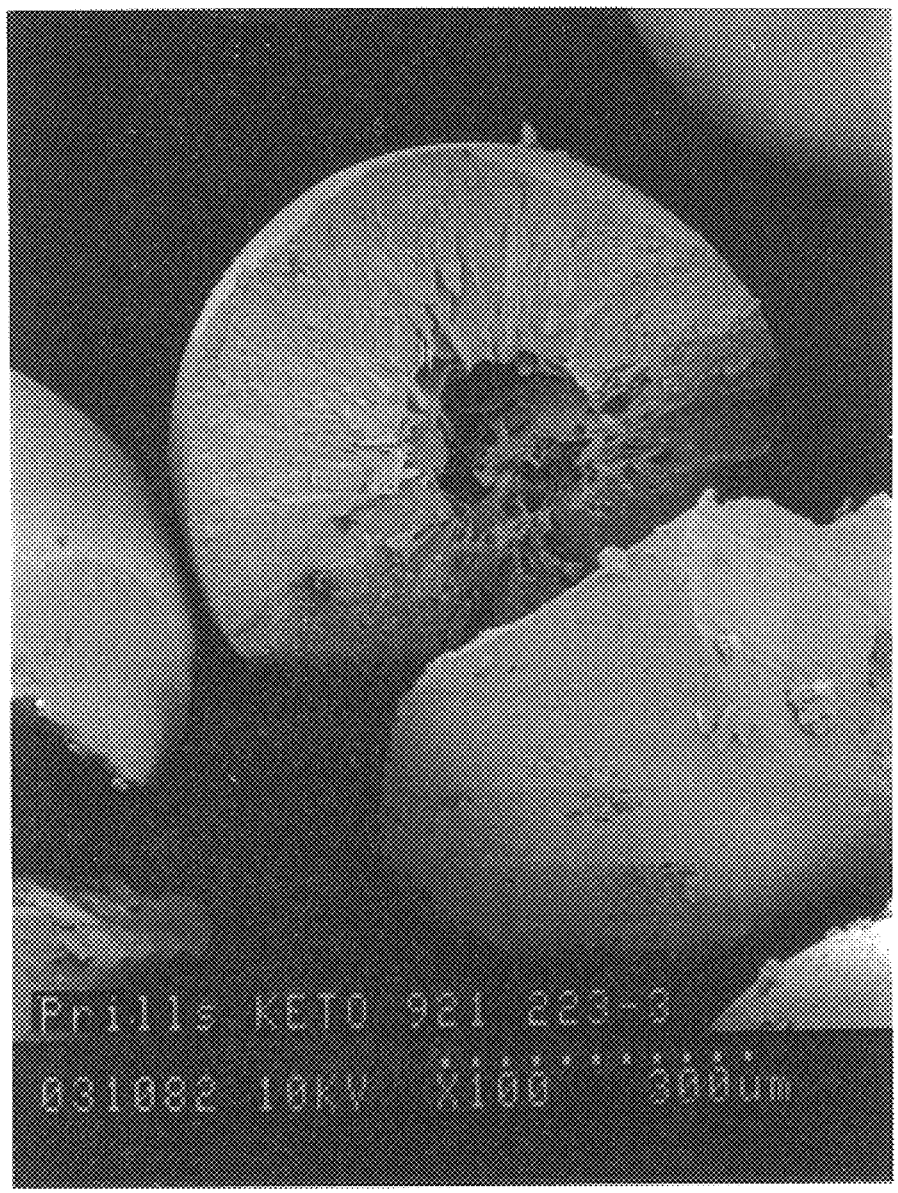

United States Patent [19]
Le Thiesse et al.

[11] Patent Number: 6,074,580
[45] Date of Patent: Jun. 13, 2000

[54] METHOD FOR THE PREPARATION OF PEARLS AND PEARLS OBTAINED CONTAINING AN ACTIVE INGREDIENT WITH AN UNDEFINED CRYSTALLIZATION POINT

[75] Inventors: Jean-claude Le Thiesse, Saint Etienne; Michel Deleuil, Antony, both of France

[73] Assignee: Aventis Pharma SA, Anthony Cedex, France

[21] Appl. No.: 08/760,155

[22] Filed: Dec. 3, 1996

Related U.S. Application Data

[63] Continuation-in-part of application No. PCT/FR95/00717, Jun. 1, 1995.

[30] Foreign Application Priority Data

Jun. 3, 1994 [FR] France .................................... 94 06842

[51] Int. Cl.⁷ ........................................ B29B 9/00
[52] U.S. Cl. ................................. 264/14; 264/9; 264/13; 427/2.14
[58] Field of Search ..................................... 264/9, 13, 14; 427/2.14

[56] References Cited

U.S. PATENT DOCUMENTS 5,188,838  2/1993  Deleuil et al. .......................... 424/451

*Primary Examiner*—David W. Wu
*Assistant Examiner*—Ling-Siu Choi
*Attorney, Agent, or Firm*—Ross J. Oehler

[57] ABSTRACT

Pearls of an active principle exhibiting an indefinite crystallization point, wherein said pearls exhibit a prolonged, immediate or combination release profiles, are made by melting the active principle and a crystallization excipient to create a molten mixture; introducing the mixture into feed receptacles of a prilling tower; passing the mixture through a nozzle which is vibrated to form pearls; and allowing the pearls to fall in the tower countercurrentwise to cold air, where the tower is provided with a fluidized bed proximate the bottom of the tower and the temperature conditions of the said fluidized bed are maintained depending on the release profile desired.

9 Claims, 2 Drawing Sheets

METHOD FOR THE PREPARATION OF PEARLS AND PEARLS OBTAINED CONTAINING AN ACTIVE INGREDIENT WITH AN UNDEFINED CRYSTALLIZATION POINT

CROSS-REFERENCE TO RELATED APPLICATIONS

This application is a continuation-in-part of International Application No. PCT/FR95/00717, filed Jun. 1, 1995, which application, in turn, is based on French Patent Application No. FR94/06842, filed Jun. 3, 1994.

The present invention relates to a new process for the preparation of pearls of a compound exhibiting an indefinite crystallization point, exhibiting a fast and/or prolonged release profile. It also relates to the pearls obtained by the process.

According to U.S. Pat. No. 5,188,838 it is known to prepare pearls of an arylpropionic acid derivative exhibiting an indefinite crystallization point, especially ketoprofen, by a process which consists in mixing, in molten form, the active principle with a pharmaceutical excipient, in forcing the molten mass to pass through a nozzle which is subjected to vibration, in allowing the pearls formed to fall in a tower, countercurrentwise to a gas, and in then collecting the pearls formed in the bottom of the tower.

A compound exhibiting an indefinite crystallization point is intended to mean a phenomenon known by the name of supercooling, the melting point of the compound is completely precise but its crystallization point is not. In fact, crystallization, for example of ketoprofen, as a pure chemical product, requires several days, above all if the molten mass is placed in a refrigerator. However, when a mixture containing ketoprofen and one or more excipients passes through the tower, the drops formed solidify sufficiently before reaching the bottom of the tower, and this allows ketoprofen to be prepared in a solid spherical form. Actually, the pearl has a solid outward appearance which enables it to be handled easily, but the ketoprofen is present within in an uncrystallized form. In the absence of human intervention, the crystallization then still requires weeks to take place completely. In the abovementioned patent a fluidized bed which permits a faster crystallization of ketoprofen is optionally added at the bottom of the tower.

It has become apparent, quite astonishingly, that the chemical nature of the excipient, the weight ratio of ketoprofen to the excipient and, above all, the size of the pearl formed and the fluidization temperature of the pearls obtained have a considerable effect on the rate of release of ketoprofen from the pearl obtained.

The present invention has made it possible to prepare pearls of active principles exhibiting a supercooling phenomenon (indefinite crystallization point) which have a reproducible release profile.

Among the active principles exhibiting an indefinite crystallization point there may be mentioned, solely by way of illustration: ketoprofen, ibuprofen and acetyl-para-aminophenol.

The excipient employed within the scope of the present invention is chosen from the excipients described in U.S. Pat. No. 5,188,838 and more preferably from saturated fatty acids containing 12 to 18 carbon atoms. It is very particularly preferred to employ stearic acid.

These pearls are obtained by a process as described in U.S. Pat. No. 5,188,838, the fluidized bed which is optionally attached to the outlet of the tower is employed in strict temperature conditions. To obtain pearls with prolonged release the temperature of the bed is maintained below the temperature of onset of liquefaction of the excipient and above the glass transition temperature of the active principle to permit its crystallization. To obtain pearls with rapid release the temperature of the bed is maintained a few degrees above the temperature of onset of liquefaction of the excipient.

One of the primary objectives of the invention consists therefore of a process for the preparation of pearls of an active principle exhibiting an indefinite crystallization point, pearls exhibiting a prolonged release profile, in which the active principle exhibiting an indefinite crystallization point and a crystallization excipient are introduced into the feed receptacles of a prilling tower and the mixture is passed through a nozzle which is vibrated to form perfectly calibrated pearls which are allowed to fall in the tower countercurrentwise to cold air, characterized in that added at the bottom of the tower there is a fluidized bed whose temperature is maintained above the glass transition temperature of the active principle exhibiting an indefinite crystallization point and below the temperature of onset of liquefaction of the excipient.

A second objective of the invention consists in preparing pearls of an active principle exhibiting an indefinite crystallization point, pearls exhibiting a rapid release profile, in which the active principle exhibiting an indefinite crystallization point and a crystallization excipient are introduced into the feed receptacles of a prilling tower and the mixture is passed through a nozzle which is vibrated to form the pearls which are allowed to fall in the tower countercurrentwise to cold air, characterized in that added at the bottom of the tower there is a fluidized bed whose temperature is maintained above the temperature of onset of liquefaction of the excipient.

Glass transition temperature is intended to mean the physical phenomenon reflected especially in an abrupt change in the heat capacity of the product. The temperature at which this transition takes place can be determined by differential thermal analysis. The solid product exhibiting a phenomenon of supercooling is melted and then brought into a state of supercooling at a very low temperature (for example –50° C.). When the temperature is gradually raised again an abrupt shift appears in the baseline, which corresponds to the change in the heat capacity of the product. The temperature at which the baseline changes is called the glass transition temperature.

Temperature of onset of liquefaction of the excipient is intended to mean the temperature at which the excipient-active principle mixture, initially molten and then rapidly cooled to a temperature that is lower than the melting temperature of the excipient (minimum 20° C.) exhibits an onset of change in physical state (either dissolving of the excipient in the active principle remaining in the supercooled state or melting of the excipient) when the temperature of the sample is raised anew. This determination is performed by differential thermal analysis of the mixture.

It is quite obvious that the temperature of onset of liquefaction of the excipient depends on the concentration of the uncrystallized active principle in the mixture. Thus, in step with the crystallization of the active principle during the stage of fluidization of the pearls, the temperature of onset of liquefaction of the excipient shifts towards higher temperatures, approaching the melting temperature of the pure excipient.

For better implementation of the invention the active principle exhibiting an indefinite crystallization point and the excipient are introduced into one of the feed receptacles of the tower, the feed receptacles of the tower are maintained under an inert gas atmosphere. In the molten state both products are notably miscible and yield a homogeneous mixture. By means of two pipes the molten liquids are brought above a nozzle which is maintained in an uncooled atmosphere and which is even optionally heated. The nozzle has 1 to 50 or more perforations which have a diameter of between 20 and 5000 microns and preferably of between 250 and 800 microns. The length of the perforation is preferably between 0.5 and 10 times its diameter.

This nozzle is subjected to a high-frequency electrical vibration system (50 to 10000 hertz). The cold air which permits the solidification of the active principle exhibiting an indefinite crystallization point and of the excipient is introduced at the bottom of the tower and leaves below the nozzle at a distance of approximately L/10 in relation to the top of the tower, L being the height of the tower. The height of the tower varies between 1 meter and some ten meters, the tower may comprise in the bottom quarter of its height a frustoconical perforated skirt which centers the pearls in the fluidized bed.

At the bottom the tower has a fluidized bed, this bed is preferably of frustoconical shape equipped at the base with a distribution grid making it possible to minimize the adhesiveness to the walls and to promote wall pearl impacts with the aim of increasing the rate of solidification. The addition of this type of apparatus permits a faster solidification of the mixture between the active principle exhibiting an indefinite crystallization point and the excipient in the bead, the temperature of the bed is adjusted as a function of the nature of the desired release profile.

It has become apparent, quite astonishingly, that although the solidification of the bead is promoted by the use of a fluidized bed, depending on the temperature of use of this bed the pearls obtained have completely different behaviour.

Thus, if the temperature of the bed or that of the storage permits an at least partial liquefaction of the excipient, solid/liquid exchanges can take place and a complete redistribution of the active principle/excipient phases is experienced. Crystal growth can develop and the crystallization of the active principle results in the formation of a geodeshaped structure. The pore volume of these pearls is generally higher than 0.045 $\mu$l/g. These pearls exhibit a rapid release profile.

On the other hand, if the temperature of the bed is lower than the onset of the temperature of liquefaction of the excipient, the supercooled active principle which exhibits a high viscosity remains trapped in the matrix of solidified excipient, crystal growth cannot develop, and the active principle remains finely dispersed within the excipient. Its release will take place only in a prolonged fashion. The pearl has a nucleated internal structure.

These pearls have a release that is slower still when they consist of ketoprofen and of stearic acid with a melting point higher than 55° C. and when they have a particle size larger than 0.7 mm, preferably larger than 1 mm and still more preferably larger than 1.5 mm, that is to say when the nozzle has perforations which have a diameter larger than 0.4 mm and preferably larger than 0.8 mm. The release is also slowed down, with the same fluidization conditions, when the excipient has a higher melting point and when the ratio of active principle to excipient decreases and is preferably lower than 1. The release is slowed down when the pore volume of these pearls is lower than 0.040 $\mu$l/g.

Figure 2:
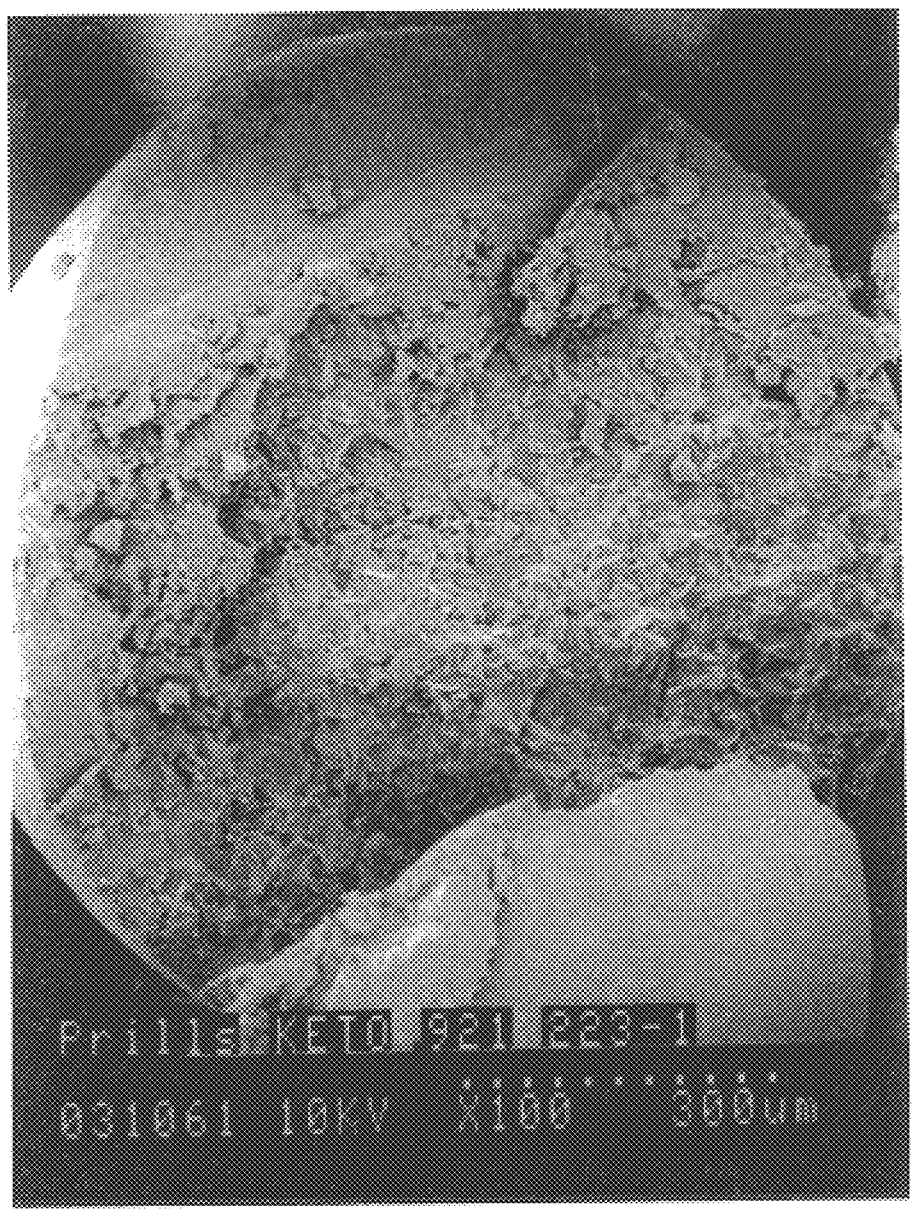

The structure of these two sorts of pearls is clearly identified in the attached photographs. FIG. 1 shows a pearl with rapid release, FIG. 2 a pearl with prolonged release.

The pearls which exhibit a nucleated structure and which have a prolonged release profile can be modified so as to exhibit dual release kinetics. In this case the pearls with prolonged release are coated with a mixture containing a hydrophilic polymer and the active principle. This hydrophilic polymer can be chosen from hydroxypropyl methyl cellulose or polyvinylpyrrolidone, it is applied notably in the form of an aqueous suspension of a mixture of pulverulent active principle and of the said polymer. It is preferred to employ hydroxypropyl methyl cellulose.

It is preferred to employ an aqueous suspension containing, by weight:

| active principle | 70–98% |
|---|---|
| hydroxypropyl methyl cellulose | 2–30% |

The suspension is prepared in a stirred reactor, for example of the Heidolph stirrer type and then in a turbine, for example of Ultra-Turrax type. A hydrophilic plasticizer such as, for example, polyethylene glycol, and a disintegrator such as carboxymethyl cellulose may be advantageously added to the aqueous suspension of active principle. These optional additives are added in quantities by weight notably of between 1 and 2% relative to the other solid compounds of the suspension.

The suspension is sprayed on to the pearls in a fluidized bed, for example of Wurster type.

The present invention will be described more fully with the aid of the following examples, which must not be considered as limiting the invention.

EXAMPLES

Ketoprofen/excipient mixtures the nature of which is shown in Table 1 are introduced into a prilling tower equipped with a melting kettle. These mixtures are introduced into the receptacle and are melted and maintained under a nitrogen atmosphere. The molten liquids are brought, by means of tubes, above a nozzle which is maintained in an uncooled atmosphere and which is even optionally heated. The nozzle employed has a single perforation which has a diameter of between 250 and 550 $\mu$m. The length of the perforation is between 0.5 and 10 times its diameter. This nozzle is subjected to a high-frequency electrical vibration system (50 to 10000 hertz). Cold air is introduced at the bottom of the tower and leaves below the nozzle at a distance which is preferably equal to approximately L/10 in relation to the top of the tower, L being the height of the tower. The height of the tower varies between 1 meter and some ten meters.

The fluidized bed which is added at the bottom of the tower is preferably a funnel-shaped fluidized bed equipped at its base with a distribution grid making it possible to minimize the adhesiveness to the walls and to promote wall-pearl impacts with the aim of increasing the rate of solidification. Table 1 shows the rates of release of ketoprofen as a function of the fluidization temperature, of the rate of temperature rise and of the stearic acid assay of the excipient employed (the stearic acid here exhibits an assay of 92%). Table 2 shows the rate of release of ketoprofen as a function of the diameter of the nozzle and of the stearic acid assay of the excipient employed.

temperature for 2 hours. The time for dissolving 80% of the ketoprofen is 3.1 hours.

Fluidization procedure 3: the pearls fluidized at −10°C. at the bottom of the tower are transferred abruptly into a second fluidized bed preheated to 55° C. The pearls are kept fluidized at this temperature for 2 hours. The time for dissolving 80% of the ketoprofen is 1.9 hours.

The pearls of Examples 1 to 6 of Table 1 are prepared by a procedure close to the fluidization procedure 1. The fluidization conditions and the time of release of 80% of the ketoprofen are shown in Table 1.

The pearls obtained in Examples 1 to 5 are coated with the mixtures shown in Table 4. The weight ratio of the ketoprofen contained in the fast layer to that in the pearl with prolonged release is 25/75. The operating conditions applied during this coating, the quantity of suspension which is sprayed and the rate of release of ketoprofen from the fast layer as shown in Table 4.

TABLE 1

MODIFICATION OF THE RATE OF RELEASE OF KETOPROFEN
AS A FUNCTION OF THE FLUIDIZATION TEMPERATURE

| Examples | Ketoprofen/ excipient composition | Nozzle diameter in mm | Temperature of onset of liquefaction of stearic acid | Fluidization and 120 minutes to reach the desired temperature | Time of release of 80% of the ketoprofen | % of release 5 h pH 6.6 |
|---|---|---|---|---|---|---|
| 1 | 70/30 | 0.25 | 30–31° C. | 1 h at −5° C. then 60 minutes to reach 45° C. + 3 h 55° C. | 1.0 h | 99% |
| 2 | 50/50 | 0.55 | 33–34° C. | 1 h at −5° C. + 6 h 35° C. | 5.5 h | 77% |
| 3 | 50/50 | 0.55 | 33–34° C. | 1 h at −5° C. + 3 h 45° C. | 5.0 h | 79% |
| 4 | 60/40 | 0.55 | 32–33° C. | 1 h at −5° C. + 4 h 45° C. | 3.50 h | 85% |
| 5 | 70/30 | 0.55 | 30–31° C. | 1 h at −5° C. then 90 minutes to reach 45° C. + 5 h 45° C. | 3.50 h | 83% |
| 6 | 50/50 | 0.55 | 33–34° C. | 1 h at −5° C. then 120 minutes to reach 45° C. + 2 h 55° C. | 4.5 h | |

The example below demonstrates the influence of the kinetics of temperature rise:

60/40 ketoprofen/stearic acid mixture
nozzle of 400 μm diameter
air temperature in the tower: −5° C.
reception of the pearls at the bottom of the tower in a fluidized bed at −10° C.

Fluidization procedure 1: the pearls fluidized at −10° C. at the bottom of the tower are brought to ambient temperature OVER some ten minutes and are fluidized at ambient temperature (approximately 18° C.) for 30 minutes. The temperature is then slowly raised to 45° C. (over approximately 2 hours) and the pearls are kept fluidized at this temperature for 4 hours. The time for dissolving 80% of the ketoprofen is 3.9 hours.

Fluidization procedure 2: the pearls are fluidized 4 hours at 45° C. The temperature is then raised over approximately one hour to 55° C. and the pearls are kept fluidized at this

TABLE 3

CHANGE IN THE RATE OF RELEASE OF KETOPROFEN
WITH THE PORE VOLUME

| Examples | Ketoprofen/55% stearic acid excipient composition | Fluidization | Storage | Pore volume | Release time |
|---|---|---|---|---|---|
| 17 | 70/30 | 2h 20° C. | 20° C. | 0.038 | 8.2 h |
| 18 | 70/30 | 1h 0° C. | 20° C. | 0.035 | 7.2 h |
| 19 | 70/30 | 2h 20° C. | 45° C. | >0.050 | 2.5 h |
| 20 | 70/30 | 1h 0° C. | 45° C. | 0.049 | 1.9 h |
| 21 | 50/50 | 2h 20° C. | 20° C. | 0.031 | 3.1 h |
| 22 | 50/50 | 2h 20° C. | 45° C. | 0.044 | 1.7 h |

TABLE 4

PEARLS OF KETOPROFEN WITH RAPID AND PROLONGED RELEASE

RAPID LAYER

| | | | | | |
|---|---|---|---|---|---|
| ketoprofen | 47.8% | 47% | 47.3% | 47.8% | 47.8% |
| HPMC | 5.3% | 5.3% | 5.2% | 5.3% | 5.3% |
| PEG 6000 | 0.5% | 0.5% | 0.5% | 0.5% | 0.5% |
| polysorbate | 0.1% | 0.1% | 0.1% | 0.1% | 0.1% |
| water | 46.3% | 47.1% | 46.9% | 46.3% | 46.4% |
| PEARLS WITH PROLONGED ACTION | | | | | |
| Weight before spraying | 400 g example 1 | 400 g example 2 | 400 g example 3 | 400 g example 4 | 400 g example 5 |
| Weight after spraying | 504 g | 475 g | 475 g | 490 g | 504 g |
| Spraying period | 5 min | 5 min | 5 min | 5 min | 5 min |
| Spraying rate | 8 g/min | 8 g/min | 8 g/min | 8 g/min | 8 g/min |
| PEARLS WITH RAPID AND PROLONGED RELEASE | | | | | |
| ketoprofen released in 15 min at pH 2.2 | 25% | 25% | 25% | 25% | 25% |
| ketoprofen released in 5 h at pH 6.6 | 100% | 87% | 87% | 91% | 89% |

What is claimed is:

1. A process for the preparation of pearls of an active principle exhibiting an indefinite crystallization point, wherein said pearls exhibit a prolonged release profile, comprising the steps of melting the active principle and a crystallization excipient to create a molten mixture; introducing the mixture into feed receptacles of a prilling tower; passing the mixture through a nozzle which is vibrated to form pearls; and allowing the pearls to fall in the tower countercurrentwise to cold air, said cold air being at a first temperature which causes supercooling of said pearls, wherein the tower is provided with a fluidized bed proximate the bottom of the tower, wherein said fluidized bed is maintained at a second temperature that is higher than said first temperature. said second temperature being above the glass transition temperature of the active principle and below the temperature of onset of liquefaction of the excipient.

2. A process for the preparation of pearls of an active principle exhibiting an indefinite crystallization point, where said pearls exhibit a rapid release profile, comprising the steps of melting the active principle and a crystallization excipient to create a molten mixture; introducing the mixture into feed receptacles of a prilling tower; passing the mixture through a nozzle which is vibrated to form pearls; and allowing the pearls to fall in the tower countercurrentwise to cold air, said cold air being at a first temperature which causes supercooling of said pearls, wherein the tower is provided with a fluidized bed proximate the bottom of the tower, wherein said fluidized bed is maintained at a second temperature that is higher than said first temperature, said second temperature being above the temperature of onset of liquefaction of the excipient.

3. Process of preparation according to claim 1, characterized in that the nozzle has a diameter larger than 0.4 mm.

4. Pearls obtained according to the process of claim 1, wherein said pearls have a melting point higher than 55° C. and have a diameter of at least 700 μm.

5. Pearls obtained according to the process of claim 1, said pearls having a pore volume lower than 0.040 μl/g.

6. The process of claim 1 further comprising coating said pearls with an aqueous suspension containing the active principle and a hydrophilic polymer.

7. Pearls according to claim 6, wherein the hydrophilic polymer is hydroxypropyl methyl cellulose.

8. Pearls obtained according to the process of claim 6.

9. Pearls obtained according to the process of claim 2, said pearls having a pore volume greater than 0.045 μl/g.

* * * * *